United States Patent [19]

Hevey

[11] Patent Number: 4,510,119
[45] Date of Patent: Apr. 9, 1985

[54] DIAGNOSTIC TEST BEAD TRANSFER APPARATUS

[75] Inventor: Richard C. Hevey, Paoli, Pa.

[73] Assignee: Centocor, Inc., Malvern, Pa.

[21] Appl. No.: 376,023

[22] Filed: May 7, 1982

[51] Int. Cl.³ .................. B01L 9/06; G01N 33/56
[52] U.S. Cl. ................................ 422/71; 53/297; 53/390; 53/392; 206/443; 211/74; 220/23.8; 422/102; 422/104; 436/809
[58] Field of Search ........... 422/102, 101, 104, 99, 422/71; 211/74; 220/23.8; 206/443; 53/390, 392, 297, 298, 330; 436/809

[56] References Cited

U.S. PATENT DOCUMENTS

| | | | |
|---|---|---|---|
| 3,098,721 | 7/1963 | Jewell | 422/99 |
| 3,859,671 | 1/1975 | Tomasello | 422/102 X |
| 3,905,772 | 9/1975 | Hartnett et al. | 422/102 X |
| 3,932,141 | 1/1976 | Beall et al. | 23/259 |
| 4,057,148 | 11/1977 | Meyer et al. | 211/74 |
| 4,090,850 | 5/1978 | Chen et al. | 23/259 |
| 4,154,795 | 5/1979 | Thorne | 422/99 |
| 4,207,289 | 6/1980 | Weiss | 422/65 X |
| 4,238,452 | 12/1980 | McMorrow | 422/104 |
| 4,286,637 | 9/1981 | Wilson | 422/102 X |
| 4,292,273 | 9/1981 | Butz et al. | 422/102 |

FOREIGN PATENT DOCUMENTS

32578/78  1/1978  Australia .

OTHER PUBLICATIONS

North American Biologicals, Inc. (NABI), by RIA International, Inc.-Radioimmunoassay Kit, (Photos Submitted).

Primary Examiner—Arnold Turk
Attorney, Agent, or Firm—Hamilton, Brook Smith & Reynolds

[57] ABSTRACT

An apparatus for transferring beads employed in a radioimmunoassay is disclosed. The apparatus comprises a receptacle tray 30, test tube rack 48 and plurality of test tubes 42. The receptacle tray 30 contains an array of wells 32, which may be marked individually with indicia such as numerals and colors, and two alignment holes 34 and 35. The test tube rack 48 contains an array of columns 51 in a pattern corresponding to that of the wells 32 on tray 30. Test tube rack 48 also contains two alignment pins 52 and 53 for insertion into alignment holes 34, 35. Each of the test tubes 42 are generally cylindrical but have a gradually increasing diameter from bottom to top so that they can be inserted into rack columns 51 with a friction fit.

2 Claims, 4 Drawing Figures

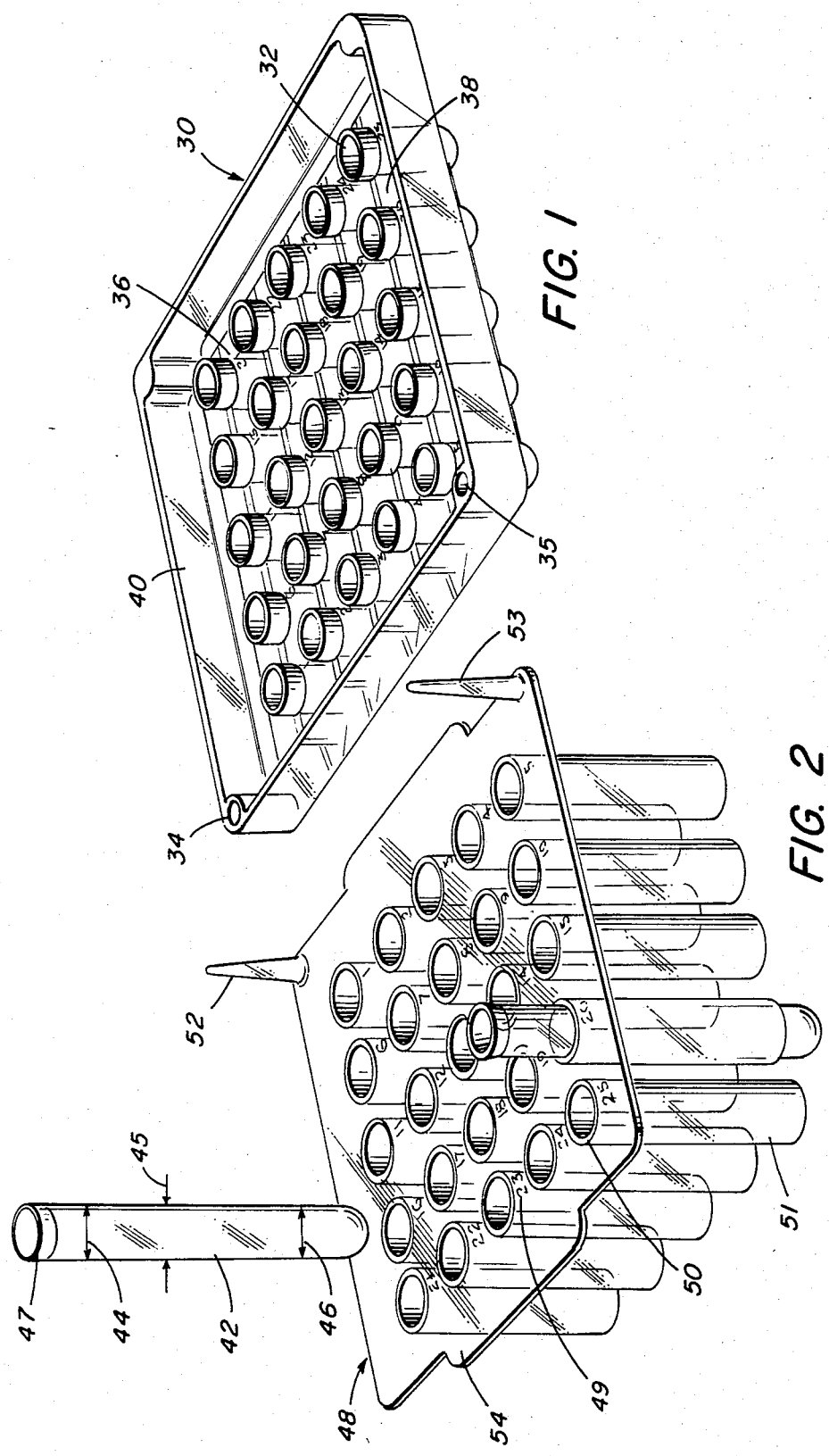

DIAGNOSTIC TEST BEAD TRANSFER APPARATUS

DESCRIPTION

1. Technical Field

This invention is in the field of immunology and particularly relates to a diagnostic test apparatus for immunoassay determination of disease associated with antigens and antibodies.

2. Background Art

Conventional radioimmunoassay is employed by hospitals and clinical laboratories for the early detection of hepatitis, and other diseases. In testing for viral hepatitis a number of polystyrene balls which have been coated with test samples and radiolabeled antibodies are placed in a receptacle tray. The receptacle tray consists of a series of wells for receiving the polystyrene balls also known as beads. Upon completion of a reaction, the beads are washed of unbound radiolabeled antibody and are measured in a suitable manner for radioactive decay.

Typically, test samples consist of antigens which may bind radiolabeled antibody. The higher amount of antigen, the larger the amount of radio-labeled antibody that binds and therefore the higher the radioactive count that is made.

In order to measure radioactivity, however, the beads must be transferred to a test tube or counting tube for insertion into the well of a radioactive counter. This can be achieved by picking up the beads one at a time and depositing them in test tubes. This process is time consuming and may lead to error if the balls are not transferred with diligence and then appropriately labeled. Various testing systems currently available attempt to correct this problem and minimize the chance of error.

A bead transfer system is currently marketed by Abbott Laboratories and is discussed in their U.S. Pat. No. 3,932,141. In the Abbott system, plastic test tubes are arranged in a matrix and are held in a cardboard box by a paper top with small holes. The cardboard box is inverted over a plastic receptacle tray supplied with the kit. After the tubes are aligned, the entire assembly is inverted and the polystyrene balls fall into the tubes. The paper top is then torn from the cardboard box and the tubes may then be removed for counting.

Although this is an improvement of picking out the styrene balls one by one, it has a number of problems. The receptacle tray may easily be placed incorrectly upon the box. Also, there is a gap between the test tubes and the tray so when the beads are transferred it is relatively easy for a ball or liquid to occasionally miss a tube. In addition, all the tubes are themselves identical, and, if more than one tube is removed from the box, they may easily be confused.

Another system is currently available from North American Biological, Inc. This Kit makes use of a receptacle tray and cardboard box much like the above-mentioned system. An addition is made, however, in that plastic pins must be inserted in the box for the box with the test tubes to sit properly upon the receptacle tray before inversion. These pins may only be inserted in one manner so that the box is not easily misaligned with the tray. It should, however, be noted that as in the above-mentioned system, the test tubes are identical and do not seat with the receptacle wells in which the polystyrene balls sit. Therefore, it is still possible for the balls to occasionally miss the test tubes and for test tubes to be confused after counting has begun. In neither of the above systems are the test tubes visible in their entirety since they sit in the cardboard box, therefore any mistakes or problems from bead transfer would not be noticed without removing the tubes individually from the box. Furthermore, defective or broken tubes will not be noted and a valuable test may have to be repeated.

In both of the above-mentioned systems, numbers are printed on the side of the box by which each tube may be identified. Such a numerical system may be misread easily when picking out a centrally located test tube.

DISCLOSURE OF THE INVENTION

This invention relates to bead transfer devices such as discussed above. The invention utilizes a receptacle tray similar to those commonly used but with two significant differences. Each of the receiving wells for the antibody coated polystyrene ball or bead is individually labeled with a number. In addition, the tray is equipped with two holes on the periphery corners for aligning a test tube rack. The test tube rack includes two pins for insertion into the above-mentioned holes of the receptacle tray.

The unique test tube rack consists of a matching array of friction fitted test tubes in resilient material. Each of the test tubes is individually labeled on the tray in a manner to match the labeling of the receptacle tray. The test tubes themselves are of resilient material and increase in diameter from the base of the tube to the top of the tube. This allows for tubes to be inserted into the test tube rack but will not allow them to pass through the rack; rather the hole in the rack forms a seat for the test tube. When the test tubes are pressed down into the rack, the rack may be inverted over the receptacle tray without the tubes falling out. The pins are aligned so that the test tube rack may only be put into position in one manner over the receptacle tray. At this point, the test tubes are pushed down onto the receiving wells.

The receiving wells of the receptacle tray are slightly tapered and of the correct diameter to mate as male pieces with the test tubes which serve as female junctions. A solid fit is therefore formed between the receiving wells and the test tubes so that there may be no leakage of liquid or polystyrene balls. The assembly is then inverted so that the test tubes are upright with the tube openings facing up. The receptacle tray can then be removed leaving the test tube rack in the upright position and labeled identically to the wells in the receptacle tray. If the test tube rack is then pushed down by tabs cast into the rack, the tubes are loosened in the rack and may be easily removed. Columns projecting down from the test tube holes form the test tube rack base and protect the test tubes from damage.

In addition to the above-mentioned identification system, the tubes have indicia upon them which make confusion of samples more difficult. In the preferred embodiment, the tubes are of five different colors. The five different colors are arranged in a consecutive sequence so that no two tubes of the same color follow one another numerically. This color coding makes it much more difficult to accidentally switch the tubes as there are only five places in a 25 tube matrix where a tube of a particular color may go whereas, with unmarked tubes, if two or three tubes are removed from the test tube rack, they may be replaced in any hole without any indicia of mistake.

In an alternate embodiment of the invention, an automatic test tube plug identification and insertion system is used. After the test tubes are released from their friction fit with the test tube rack, a flexible sheet of plastic material is aligned by the pins and placed upon the tubes. A plunger tool is then used to push precut plugs from the flexible sheet into the test tubes. The plugs are pre-numbered to match the matrix numbers disposed upon the test tube rack. The flexible sheet is then removed minus the cutout plugs and the plugged test tubes are then ready for analysis.

BRIEF DESCRIPTION OF THE DRAWINGS

FIG. 1 is a perspective view of the receptacle tray.

FIG. 2 is a perspective view of the test tube rack including two test tubes.

PREFERRED EMBODIMENT OF THE INVENTION

Figure 3:
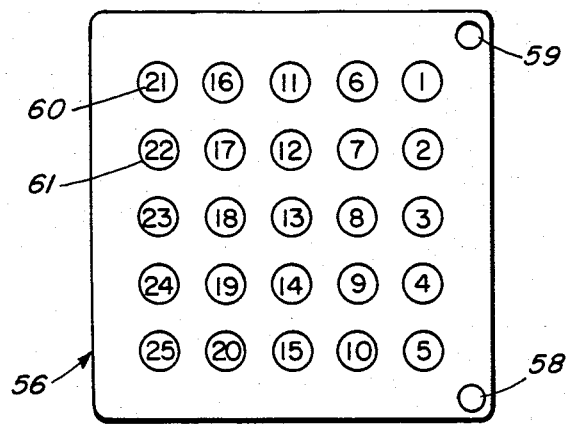
FIG. 3 is a perspective view of the test tube plug board.

The foregoing and other objects, features, and advantages of the invention will be apparent from the following more particular description of the preferred embodiments of the invention as illustrated in the accompanying drawings, in which like reference characters refer to the same parts throughout the different view. The drawings are not necessarily to scale, emphasis instead being placed upon illustrating the principles of the invention.

All the pieces in this embodiment are best constructed of translucent resilient material which allows for strength, translucency and friction fit assembly.

Referring now to FIG. 1, which is a perspective view of the receptacle tray 30, the receptacle tray has twenty-five wells 32 for receipt of test beads and is arranged in a 5×5 matrix. Each of the wells 32 is marked individually with numerals 36 so that test samples will not be confused. Also of interest, on the receptacle tray are two holes 34, 35 for the alignment of the tray with the test tube rack to be described below.

Underneath the wells 32 a stiffening member 38 adds strength to the receptacle wells and prevents breakage. The stiffening member 38 connects five wells in a row in the matrix. Also visible in this view is retaining wall 40. The retaining wall 40 provides for structural strength and ease of handling. It surrounds the matrix of wells on all four sides and projects above the height of the wells.

In FIG. 2 may be seen two of the twenty-five test tubes 42 that fit into the test tube rack. The test tubes 42 are generally cylindrical; however, the diameter at the base 46 is smaller than that at the upper portion 44. The inner diameter 44 at the upper portion is slightly larger than the outer diameter of the top of the receptacle well 32. In addition, there is a reinforcing band 47 at the opening of the test tube. The increased diameter and the reinforcing band 47 are provided so that the test tube may be pushed down onto the receptacle well and form a tight seal. The purpose of this is to ensure complete transfer from the receptacle well of the test bead without allowing accidental leakage of the bead or any liquid to an adjacent well.

Also in FIG. 2 is a perspective view of the test tube rack 48 in which the test tubes 42 are inserted. The test tube holes 50 are slightly smaller in diameter than the largest test tube outer diameter 45, hence the test tubes cannot pass through the rack but rather are retained in a friction fit assembly.

The test tube rack has two aligning pins 52, 53 to be inserted into the bead receptacle tray 30. Having two pins 52,53 in the manner shown, the test tube rack may only be inserted into the receptacle tray in one orientation. This orientation is such that the numeric markings 49 of the test tube rack will match the numeric markings 36 of the receptacle tray.

In FIG. 2 the test tube columns 51 can be seen projecting down from the holes 50 which serve as both protection for the test tubes and form a base for the test tube rack.

A review of the use of the receptacle tray and test tube rack is now in order. The twenty-five test tubes 42 are inserted into the twenty-five holes 50. Each test tube is pressed down into the hole and because of their increasing diameter, they form a friction fit with the test tube holes 50. Once the test tubes 42 have been inserted into the test tube rack 48 and forced down relatively tightly, the test tube rack is inverted. The inverted rack is placed over the receptacle tray 30. When the test tube rack is seated in position, the test tubes are individually pressed down onto the receptacle wells 32 to form tight seals. When this has been done, the entire assembly is once again turned over. The test beads and any liquid in the wells is thus transferred into the test tubes. After the assembly is inverted, the receptacle tray is removed from the test tube rack. Tabs 54 on the test tube rack 48, FIG. 2, are then pushed down to free the test tubes from their friction fit. The rack base is formed by the bottom columns 51 of the test tube wells 50. The test tubes are now free to be easily removed from the test tube rack 48 as the need arises.

It should be noted that the markings on the test tube rack are identical to the markings of the receptacle tray so that no test samples will be confused. In addition, the test tubes have their own indicia included. In this embodiment, the test tubes are of five different colors. In this way, color coded test tubes may not be easily confused. For example, all the test tubes in one row at right angles to the numerical sequence starting with 1 might be blue and all the test tubes in the row starting with 2, red, and so on. In this case, two contiguous test tubes, each located in a different row, could not be incorrectly replaced on the test tube tray without an obvious color misplacement.

In FIG. 3 is shown a test tube plug board 56 which is placed over the test tubes once they have been released from the friction fit with the test tube rack 48. The two holes 58, 59 are aligned with the two pins 52, 53 on the test tube rack. The numerical indicia, 60, 61, etc., face up when the plug board 56 has been properly positioned. In this way, such indicia are visible and match the numerical indicia of the test tube rack 48. The plugs 61 have been die cut from the polyurethane plug board but not removed from that board.

Figure 4:
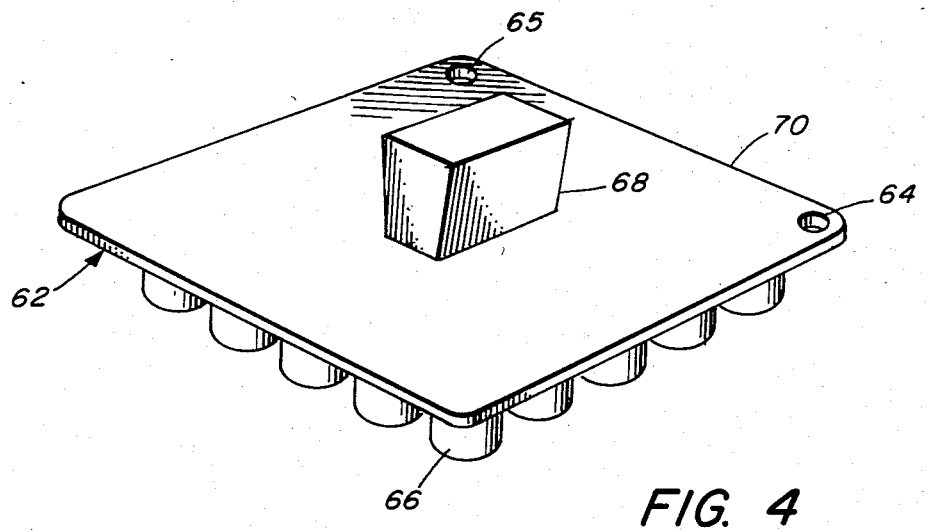
FIG. 4 is a perspective view of the test tube plug insertion tool.

In FIG. 4 is shown the test tube plug insertion tool 62 which pushes the plugs from the plug board 56 into the test tubes 42. The insertion tool 62 is constructed of a plastic sheet 70 onto which the handle 68 and the various plungers 66 are attached. The tool's matrix of plungers 66 matches the matrix of test tubes and plugs previously described. The holes 64, 65 are aligned on the pins 52, 53 which protrude above the plug board. As the tool is pushed down by the handle 68, the plungers 66 force the plugs from the plug board into the test tubes.

After the plugs have been inserted into the test tubes, the insertion tool 62 and the plug board 56 are removed from the pins. The pins 52, 53 themselves may then be removed from the test tube rack by snipping or breaking. What remains are twenty-five test tubes in a matrix each labeled by means of its plug 60, 61, etc., its color and the number 49 on the test tube rack itself. In this way the combined system leaves very little room for confusion or mistake in the analysis of the immunoassay beads.

While the invention has been particularly shown and described with reference to preferred embodiments thereof, it will be understood by those skilled in the art that various changes in form and detail may be made therein without departing from the spirit and scope of the invention as defined by the intended claims. For example, the indicia marking the test tubes may easily be changed to letters or different colors or various other markings on the test tubes themselves. Alternately, a different set of aligning pins and pilot holes might be devised.

I claim:
1. A diagnostic test apparatus for use in an immunoassay, comprising:
   a. a receptacle tray of resilient material having a plurality of wells for receiving samples,
   b. said receptacle tray having at the least one pilot hole,
   c. a test tube rack of resilient material having a plurality of holes for insertion of test tubes, said test tube rack having at least one pin for insertion into the pilot hole of the receptacle tray,
   d. test tubes of generally cylindrical shape composed of resilient material, said test tubes having a varying outside diameter so as to form a friction fit when pressed into test tube rack,
   e. indicia of marking of correlating nature present on said test tube rack and receptacle tray, and
   f. a plunger and precut plugboard means for inserting test tube plugs into several test tubes essentially simultaneously.

2. A diagnostic test apparatus as claimed in claim 1 further characterized by indicia of marking on each test tube plug matching the markings on the test tube rack.

* * * * *